(12) United States Patent
Hayashi et al.

(10) Patent No.: US 7,311,093 B2
(45) Date of Patent: Dec. 25, 2007

(54) ELEMENT CRACK DETECTING APPARATUS AND METHOD FOR OXYGEN SENSOR

(75) Inventors: Tsutomu Hayashi, Anjo (JP); Hajime Nomura, Okazaki (JP); Yoshitaka Uematsu, Anjo (JP); Toshiaki Iwashita, Kariya (JP); Kensuke Mizui, Kariya (JP)

(73) Assignee: Denso Corporation, Kariya, Aichi-pref. (JP)

( * ) Notice: Subject to any disclaimer, the term of this patent is extended or adjusted under 35 U.S.C. 154(b) by 0 days.

(21) Appl. No.: 11/482,820

(22) Filed: Jul. 10, 2006

(65) Prior Publication Data

US 2007/0012564 A1 Jan. 18, 2007

(30) Foreign Application Priority Data

Jul. 13, 2005 (JP) ............................. 2005-204506

(51) Int. Cl.
*F02D 41/22* (2006.01)
*F02D 41/14* (2006.01)
*G01N 27/409* (2006.01)

(52) U.S. Cl. ...................... 123/688; 73/1.06; 123/690; 204/401

(58) Field of Classification Search ................ 123/479, 123/688, 690; 73/1.06, 23.32, 118.1; 701/109; 702/183, 185; 204/401
See application file for complete search history.

(56) References Cited

U.S. PATENT DOCUMENTS

| | | | |
|---|---|---|---|
| 4,638,658 A | 1/1987 | Otobe ....................... 73/117.3 |
| 5,298,865 A | 3/1994 | Denz et al. .................. 324/509 |
| 5,781,878 A | 7/1998 | Mizoguchi et al. ......... 701/109 |
| 6,304,813 B1 * | 10/2001 | Ikeda et al. ................. 701/109 |
| 6,978,653 B2 * | 12/2005 | Hattori ....................... 73/1.06 |
| 7,073,320 B2 * | 7/2006 | Moritsugu et al. .......... 123/688 |
| 2006/0277971 A1 * | 12/2006 | Tashiro et al. ............... 73/1.06 |

FOREIGN PATENT DOCUMENTS

| | | |
|---|---|---|
| JP | 6-3158 | 1/1994 |
| JP | 6-23556 | 3/1994 |
| JP | 11-166438 | 6/1999 |
| JP | 11-201935 | 7/1999 |
| JP | 11-218045 | 8/1999 |
| JP | 2000-241381 | 9/2000 |

* cited by examiner

*Primary Examiner*—T. M Argenbright
(74) *Attorney, Agent, or Firm*—Nixon & Vanderhye P.C.

(57) ABSTRACT

An element crack detecting apparatus for an oxygen sensor detects a sensor output voltage for an abnormality detection period after a fuel cut-off is started during operation of an engine. When the output voltage becomes negative, an abnormality counter is counted up. When the abnormality counter value reaches a determination value, it is determined that the element crack is present. The abnormality detection period is variably set in response to an engine rotational speed, an intake air quantity and the mixture state immediately before the fuel cut-off is effected. The determination value is variably set in response to the oxygen sensor temperature and the mixture state immediately before the fuel cut-off is effected. Further, the determination value is variably set in response to a magnitude of the negative voltage of the oxygen sensor.

26 Claims, 8 Drawing Sheets

ELEMENT CRACK DETECTING APPARATUS AND METHOD FOR OXYGEN SENSOR

CROSS REFERENCE TO RELATED APPLICATION

This application is based on Japanese Patent Application No. 2005-204506 filed on Jul. 13, 2005, the disclosure of which is incorporated herein by reference.

FIELD OF THE INVENTION

The present invention relates to element crack detecting apparatus and method for an oxygen senor and, in particular, to a technology of detecting an element crack abnormality for a concentration cell oxygen sensor disposed in an exhaust system of an engine.

BACKGROUND OF THE INVENTION

A vehicle is conventionally provided with an engine control apparatus which is adapted to perform such an air-fuel ratio feedback control as to determine a fuel injection quantity to an engine so that an air-fuel ratio of an air-fuel mixture be controlled to a target value based upon an output signal of an air-fuel ratio sensor disposed in an exhaust system of the engine (e.g., JP 2000-241381A).

In addition, a concentration cell oxygen sensor is known as an air-fuel ratio sensor. This concentration cell oxygen sensor is, as exemplified in FIG. 11, constructed in such a manner that electrodes 103 and 105 made of platinum or the like are located respectively on the outer surface and the inner surface of a cup-shaped solid electrolyte 101 made of zirconia or the like. The solid electrolyte 101 and the electrodes 103, 105 form a detecting element. The outer side of the cup-shaped solid electrolyte 101 is exposed to exhaust gases and air is introduced inside the cup-shaped solid electrolyte 101. Accordingly, the electrode 103 located on the outer surface of the solid electrolyte 101 serves as an exhaust-side electrode facing exhaust gases and the electrode 105 located on the inner surface of the solid electrolyte 101 serves as an atmosphere-side electrode facing an atmosphere.

Figure 11:
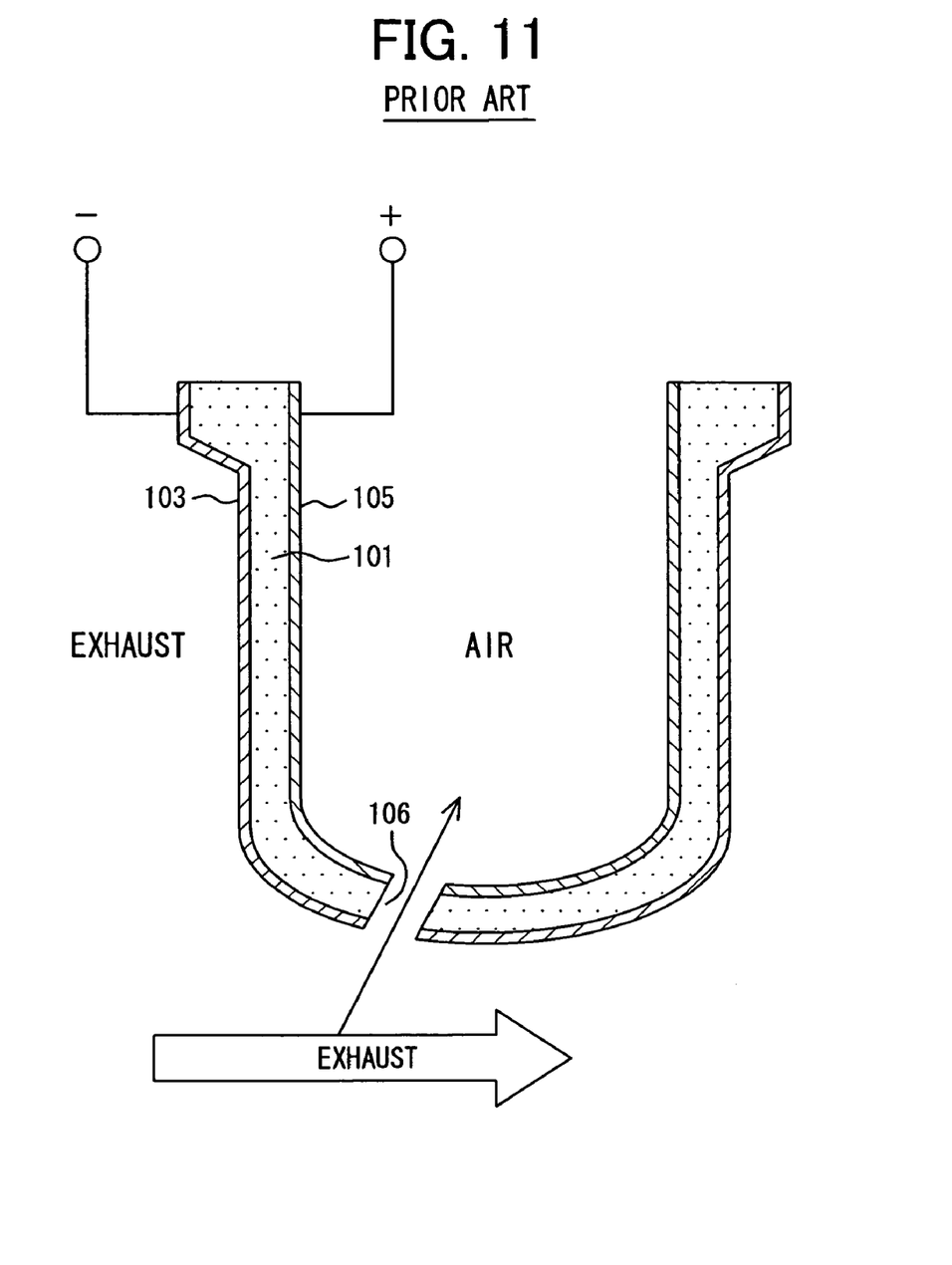
FIG. 11 is a schematic cross sectional view of a conventional oxygen sensor.

In such a concentration cell oxygen sensor, a density difference between the oxygen density of the exhaust-side electrode 103 and the oxygen density of the atmosphere-side electrode 105 produces an electromotive force and a potential difference between the electrodes is detected as an output voltage of the oxygen sensor. The output voltage changes sharply or in stepwise in the vicinity of a stoichiometric air-fuel ratio. In a range richer in fuel than the stoichiometric air-fuel ratio, the output voltage becomes 1 V and in a range leaner in fuel than the stoichiometric air-fuel ratio, the output voltage becomes about 0 V (e.g., JP-2000-241381A). In this case, electrons flow from the exhaust-side electrode 103 to the atmosphere-side electrode 105 to produce the electromotive force. Therefore, the output voltage can be produced as a potential difference on the basis of the exhaust-side electrode 103 as a reference.

The solid electrolyte 101 becomes in an activated state in which the solid electrolyte 101 serves as an oxygen ion conductor at a temperature more than a certain activation temperature (e.g., 300° C.) and produces an electromotive force as a concentration cell in response to a difference in oxygen density between the inner surface (atmosphere-side face) and the outer surface (exhaust-side face) of the solid electrolyte 101. Therefore, the solid electrolyte 101 is heated to the activation temperature by a heater so that it may become operative at earlier time. Even if the solid electrolyte 101 is thus activated, this oxygen sensor will not operate if the sensor element including the solid electrolyte 101 cracks.

SUMMARY OF THE INVENTION

It is therefore an object of the present invention to provide element crack detecting apparatus and method for an oxygen sensor, which can detect an element crack abnormality for an oxygen sensor.

The present invention is based on the following analysis on the concentration cell oxygen sensor shown in FIG. 11.

In the concentration cell oxygen sensor, a space defined in the side of the exhaust-side electrode 103 is set as an exhaust-side and a space defined in the side of the atmosphere-side electrode 103 is set as an atmosphere-side. In this case, when an element crack 106 (in detail, a crack of an element portion composed of the solid electrolyte 101 and the electrodes 103 and 105), is generated, the exhaust gases flow from the cracked portion into the atmosphere-side. As a result, the oxygen density in the atmosphere-side is lowered than in the case of no crack in the element.

Therefore, when the fuel cut-off to the engine is effected for instance and the exhaust gases having the same level in oxygen density with the atmosphere reach the oxygen sensor, the oxygen density at the exhaust-side of the oxygen sensor becomes substantially equal to that of the atmosphere. Thus, the oxygen density at the exhaust-side becomes higher than that at the atmosphere-side. As a result, the output voltage of the oxygen sensor becomes negative, that is, reversed. That is, the potential of the exhaust-side electrode 103 becomes higher than that of the atmosphere-side electrode 105 and the negative voltage is outputted as a sensor output relative to the exhaust-side electrode 103 as a reference.

Accordingly, it is possible to detect the output voltage of the oxygen sensor to determine whether the output voltage becomes reversed, and thereby determine whether the element abnormality occurs based upon the determination result. The output voltage of the oxygen sensor may be detected at fixed time point after a fuel cut-off to the engine starts to be effected.

It is preferred to provide a delay in detecting the output voltage of the oxygen sensor after the fuel cut-off, because the output voltage will change with delay due to exhaust flow from the engine to the oxygen sensor. It is also preferred to variably set the delay and/or a crack abnormality detection period based on engine conditions, because the exhaust flow speed varies with the engine conditions.

BRIEF DESCRIPTION OF THE DRAWINGS

The above and other objects, features and advantages of the present invention will become more apparent from the following detailed description made with reference to the accompanying drawings, in which like parts are designated by like reference numbers and in which.

DETAILED DESCRIPTION OF THE PREFERRED EMBODIMENT

First Embodiment

Figure 1:
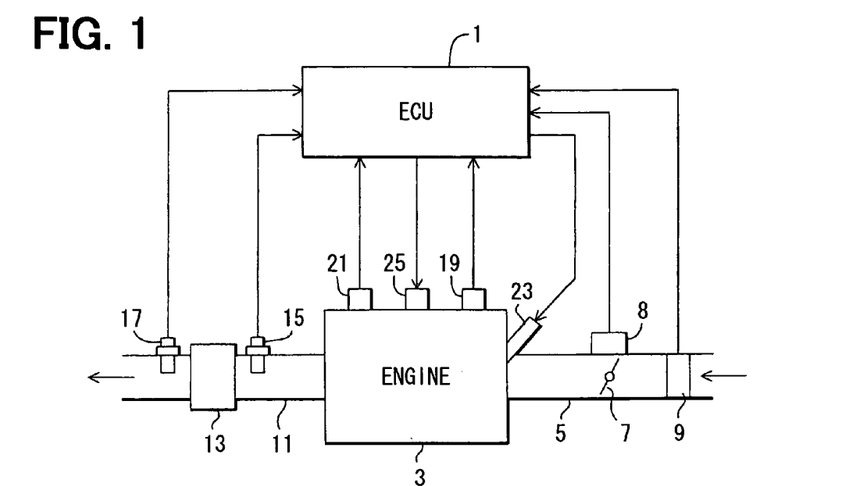
FIG. 1 is a schematic block diagram showing an engine control system including an electronic control unit (ECU) and peripheral components according to an embodiment of the present invention.

Referring first to FIG. 1, an electronic control unit (ECU) 1 is provided for an internal combustion engine 3 in an engine control system. In this system, a throttle valve 7 and a throttle position sensor 8 for detecting a throttle position (opening) of the throttle valve 7 are disposed in an intake passage 5 of the engine 3. Further, an air flow meter 9 as a sensor for detecting an intake air quantity to the engine 3 is disposed in the intake passage 5 at a location upstream the throttle valve 7.

A catalyst converter 13 for purifying exhaust gases is disposed in an exhaust passage 11 of the engine 3. Oxygen sensors 15 and 17 as air-fuel ratio sensors each are disposed in the exhaust passage 11 at a location upstream the catalyst converter 13 and at a location downstream the catalyst converter 13.

In addition, a rotation sensor 19 for detecting an engine rotational speed, a coolant water temperature sensor 21 for detecting a coolant water temperature and the like are attached to the engine 3.

Signals from various sensors including each of the above sensors 8, 9, 15, 17, 19, 21 and signals from various switches including an ignition switch (not shown) are inputted to the ECU 1. The ECU 1 detects an operating condition of the engine 3 based upon the signals and drives various actuators such as an injector 23 for fuel injection and an ignition apparatus 25 based upon the detection result, thereby operating the engine 3 at an optimum condition. The oxygen sensor 15 at a location upstream the catalyst converter 13 is a limit current oxygen sensor generating a limit current in accordance with an air-fuel ratio and the oxygen sensor 17 at a location downstream the catalyst converter 13 is a concentration cell oxygen sensor explained with reference to FIG. 11.

The ECU 1 is adapted to perform an air-fuel ratio feedback control on the basis of the detection result of an air-fuel ratio detected based upon the upstream-side oxygen sensor 15 and correct a fuel injection quantity (i.e., air-fuel ratio) by using the detection result of the air-fuel ratio (rich or lean air-fuel ratio) detected based upon the downstream-side oxygen sensor 17. That is, the downstream-side oxygen sensor 17 is used as a sub-sensor. Further, The ECU 1 is adapted to detect an element crack abnormality of the downstream-side oxygen sensor 17.

Figure 2:
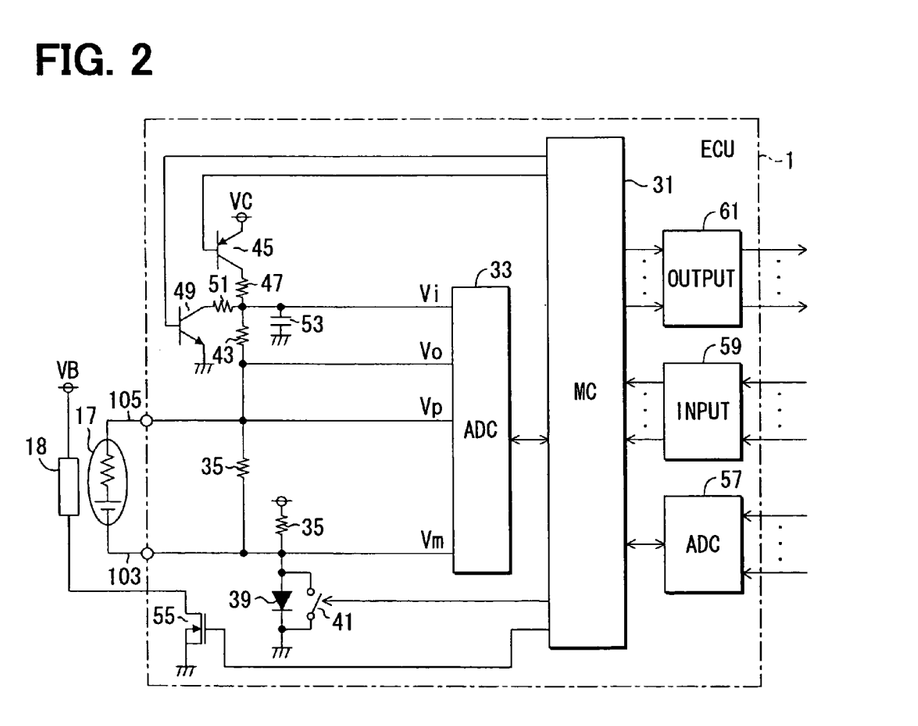
FIG. 2 is a circuit diagram showing a construction of the ECU.

As shown in FIG. 2, the ECU 1 is provided with a microcomputer 31 for performing control of the engine 3 and also executing the processing for performing an element crack detection of the oxygen sensor 17, an A/D converter 33 for inputting an analog signal of a detection object in regard to the oxygen sensor 17 to the microcomputer 31 and a resistor 35 for voltage stabilization connected between an exhaust-side electrode 103 made of platinum and an atmosphere-side electrode 105 made of platinum of the oxygen sensor 17. The microcomputer 31 includes a CPU, a ROM, a RAM and the like therein. In addition, a resistance value of the resistor 35 is set as a very large value such as several MΩ in order to avoid an adverse influence to operations of the oxygen sensor 17.

A voltage Vp of the atmosphere-side electrode 105 and a voltage Vm of the exhaust-side electrode 103 of the oxygen sensor 17 as A/D conversion objects are inputted to the A/D converter 33.

In addition, for increasing the potential of the exhaust-side electrode 103 of the oxygen sensor 17 to the potential greater than the ground level (i.e., 0 V as the potential of the ground line) of the ECU 1, the ECU 1 is provided with a resistor 37 for pull-up connected between the exhaust-side electrode 103 and a constant voltage VC (5 V in the embodiment) and a diode 39 having an anode connected to the exhaust-side electrode 103 and a cathode connected to the ground line. Further, the ECU 1 is provided with a switch 41 for short-circuiting the anode and the cathode of the diode 39 in response to a command from the microcomputer 31.

Therefore, when the switch 41 is in an OFF state, the potential of the exhaust-side electrode 103 increases by the forward voltage (approximately 0.7 V) of the diode 39 from the ground level. On the other hand, when the switch 41 is in an ON state, the potential of the exhaust-side electrode 103 becomes 0 V, equal to the ground level.

The ECU 1 is further provided with a circuit for measuring element impedance (in detail, impedance of the solid electrolyte 101) of the oxygen sensor 17. The circuit includes a shunt resistor 43, a PNP transistor 45, a resistor 47, a NPN transistor 49, a resistor 51 and a capacitor 53. The shunt resistor 43 has an end connected to the atmosphere-side electrode 105. The PNP transistor 45 has an emitter connected to a constant voltage VC. The resistor 47 has one end connected to a collector of the transistor 45 and the other end connected to the opposing side (upstream side) to the atmosphere-side electrode 105 of the shunt resistor 43. The NPN transistor 49 has an emitter connected to the ground line. The resistor 51 has one end connected to a collector of the transistor 49 and the other end connected to the upstream side of the shunt resistor 43. The capacitor 53 connected between the upstream side of the shunt resistor 43 and the ground line to form an integral circuit with the resistances 47 and 51. Voltages Vi and Vo at both ends of the shunt resistor 43 are taken in the microcomputer 31 through the A/D converter 33. The transistors 45 and 49 are switched on/off by the microcomputer 31.

The element impedance may be measured by such circuits are known (JP 11-201935A). That is, the microcomputer 31 turns on the transistor 45 to instantly change an applied voltage to the oxygen sensor 17. The microcomputer 31 also detects a difference between a sensor current (current flowing in the oxygen sensor 17) before changing the applied current and a sensor current at a point a predetermined time elapses after changing the applied voltage, from the voltages Vi and Vo at both ends of the shunt resistor 43. The microcomputer 31 calculates the element impedance based upon the difference. In addition, the transistor 49 is turned on for discharging electrical charges accumulated in the capacitor 53 after the measurement of the element impedance is finished.

A heater 18 for heating the oxygen sensor 17 is located near the oxygen sensor 17. The heater 18 is connected at one end to a battery voltage VB (usually 12 V) and at the other end to one end of MOSFET 55 provided in the ECU 1. The MOSFET 55 has the other end grounded through a drain. Further, the microcomputer 31 performs known heater control for modulating supply current to the heater 18 by duty-controlling the MOSFET 55 so that the element impedance of the oxygen sensor 17 measured by the above order is made to be a value by which the oxygen sensor 17 is considered to be in an activated state.

Further, the ECU 1 is provided with an A/D converter 57, an input circuit 59 and an output circuit 61. The A/D converter 67 is for inputting analog signals other than signals related to the oxygen sensor 17 among the signals from the above various sensors to the microcomputer 31. The input circuit 59 is for inputting non-analog signals among the signals from the above various sensors and signals from the above various switches to the microcomputer 31. The output circuit 61 is for outputting drive signals to the various actuators according to commands from the microcomputer 31.

In the ECU 1, the microcomputer 31 detects the voltage Vp at the atmosphere-side electrode and the voltage Vm at the exhaust-side electrode of the oxygen sensor 17 with the A/D converter 33. It then calculates a difference between both voltages Vp and Vm (=Vp−Vm) as an output voltage of the oxygen sensor 17. In fact, the potential of the atmosphere-side electrode 105 to the potential of the exhaust-side electrode 103 in accordance with a difference in oxygen density between both the electrodes is detected as an output voltage of the oxygen sensor 17. In addition, the microcomputer 31 determines whether the state of the air-fuel mixture is rich or lean, based upon the detected output voltage of the oxygen sensor 17 and corrects a fuel injection quantity in response to the determination result. Oxygen ions travel from the atmosphere-side electrode 105 to the exhaust-side electrode 103 at a normal time. As a result, a positive value on the basis of a reference of the exhaust-side electrode 103 is detected as an output voltage of the oxygen sensor 17. At this point, when an air-fuel ratio of the mixture is richer than the stoichiometric air-fuel ration, a travel amount of the oxygen ions is large to output a high value as the output voltage. On the other hand, when an air-fuel ratio of the mixture is leaner than the stoichiometric air-fuel ration, a travel amount of the oxygen ions is low to output a value close to zero as the output voltage.

Further, when a specific fuel cut-off condition (e.g., deceleration) is met during the operating of the engine 3, the microcomputer 31 effects the fuel cut-off for forcibly stopping the fuel injection to the engine 3. In an abnormality detection period (Tab in FIG. 4) after the fuel cut-off is started, the microcomputer 31 determines whether the output voltage of the oxygen sensor 17 becomes a negative voltage and then determines based upon the determination result whether element crack abnormality occurs in the oxygen sensor 17.

The embodiment has two kinds of fuel cut-off conditions. One is for fuel saving that an operation amount of an accelerator pedal by a driver is zero and also an engine rotational speed is more than a prescribed fuel cut-off rotational speed NC1. When this condition is met and the fuel cut-off for fuel saving is effected, the condition (fuel resumption condition) that the fuel cut-off stops and the state where fuel is again injected to the engine 3 returns lies in that the operation amount of the accelerator pedal by a driver changes from zero or the engine rotational speed becomes less than a fuel resumption rotational speed NR1, which is smaller than the fuel cut-off rotational speed NC1. The other is for engine protection (revolution limit) that an engine rotational speed is more than a fuel cut-off rotational speed NC2 close to the revolution limit. When this condition is met and the fuel cut-off for fuel saving is effected, the fuel resumption condition is that the engine rotational speed becomes less than a fuel resumption rotational speed NR2, which is smaller than the fuel cut-off rotational speed NC2.

Figure 3:
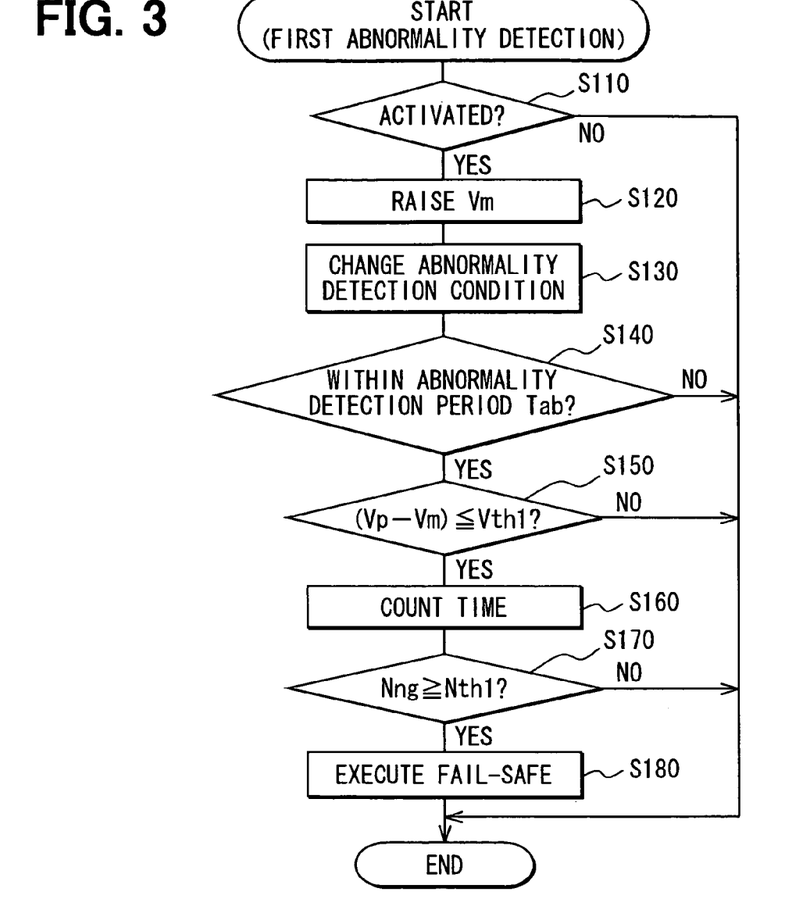
FIG. 3 is a flow chart showing abnormality detection processing.

The microcomputer 31 is programmed to detect element crack abnormality of the oxygen sensor 17 as shown in FIG. 3 in addition to execute other normal engine control.

When the microcomputer 31 starts execution of the abnormality detection processing, first at step S110 it is determined whether the oxygen sensor 17 is in an activated state. When it is determined that the oxygen sensor 17 is not in an activated state, the microcomputer 31 ends the abnormality detection processing. On the other hand, when it is determined that the oxygen sensor 17 is in an activated state, the process proceeds to step 5120, wherein the switch 41 which has been in an ON state is changed and maintained to be in an OFF state That is, the switch 41 is maintained to be in an ON state until it is determined at step S110 that the oxygen sensor 17 is in an activated state. When it is determined at step S110 that the oxygen sensor 17 is in an activated state, the microcomputer 31 makes the switch 41 be in an OFF state. When the switch 41 is in an OFF state, the diode 39 becomes effective, so that the potential Vm of the exhaust-side electrode 103 of the oxygen sensor 17 increases by the forward voltage of the diode 39 from the ground level.

In addition, it is determined at activated state determination processing (not shown) different from that in FIG. 3 whether the oxygen sensor 17 is in an activated state. As for the order of the activated state determination processing, when power is supplied to the ECU 1 by ON of the ignition switch, the power to the heater 18 is started and also an output voltage of the oxygen sensor 17 is detected. Then, it is determined whether the output voltage is a positive predetermined value. When the output voltage reaches the predetermined value, it is determined that the oxygen sensor 17 is in an activated state. In addition, at step S110 it is determined whether the oxygen sensor 17 is in an activated state by referring to the determination result of such activated state determination processing.

Further, in the embodiment, until it is determined that the oxygen sensor 17 is in an activated state by the above activated state determination processing, the potential Vm of the exhaust-side electrode 103 of the oxygen sensor 17 is maintained to be in the ground level (at step S110: NO).

When it is determined that the oxygen sensor 17 is in an activated state by the above activated state determination processing, the potential Vm of the exhaust-side electrode 103 of the oxygen sensor 17 is forced to be increased to the potential higher by the forward voltage of the diode 39 than the ground level (at step S110: YES→S120).

After the switch 41 is turned off at step S120, at next step S130 abnormality detection condition changing processing for variably setting time T1 and time T2 and determination values Vth1 and Nth1 to be described later is executed. The content of the abnormality detection condition changing processing will be in detail described later.

Figure 4:
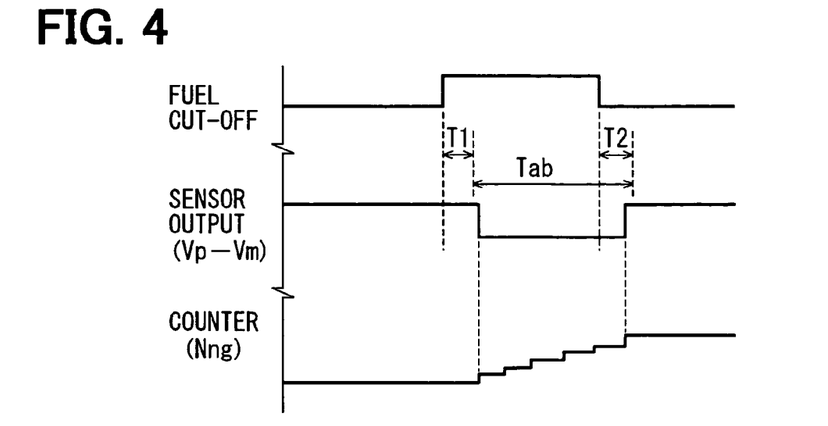
FIG. 4 is a time chart showing operations of the abnormality detection processing.

Next, at step S140 it is determined whether an engine operating condition at the present time is within an abnormality detection period Tab for the oxygen sensor 17. When the engine operating condition at the present time is not within the abnormality detection period Tab, the abnormality detection processing ends. When the engine operating condition at the present time is within the abnormality detection period Tab, the process proceeds to step S150. The abnormality detection period Tab is, as shown in FIG. 4, a period from a point when first delay time T1 elapses after the starting of the fuel cut-off to a point when second delay time T2 elapses after the ending of the fuel cut-off. The delay times T1 and T2 are provided because the exhaust gases take some time to flow in the exhaust passage 11 from the engine 3 to the oxygen sensor 17 through the catalyst converter 13.

At step S150 an output voltage of the oxygen sensor 17 (Vp−Vm) is calculated and also it is determined whether the output voltage is less than the negative voltage determination value Vth1. When the output voltage is not less than the negative voltage determination value Vth1, the oxygen sensor 17 is considered as normal and the abnormality detection processing ends. When the output voltage is less than the negative voltage determination value Vth1, it is determined that the output voltage is a negative voltage and the oxygen sensor 17 is considered as abnormal. The process proceeds to step S160.

At step S160, an abnormality counter counts time Nng during a period when it is determined that the output voltage of the oxygen sensor 17 is the negative voltage. At step S170 it is determined whether a value Nng of the abnormality counter is more than a negative voltage continuation time determination value Nth1. When the value Nng of the abnormality counter is not more than the time determination value Nth1, the abnormality detection processing ends. When the value Nng of the abnormality counter is more than the time determination value Nth1, it is determined that the element crack abnormality occurs in the oxygen sensor 17 and the process proceeds to step S180.

At step A180 the following failsafe processing is executed. For example, abnormality information showing that the element crack abnormality occurs is stored in a rewritable non-volatile memory or a backup RAM with a power source or a warning display showing occurrence of the abnormality is made. Thereafter, the abnormality detection processing ends.

That is, in this abnormality detection processing, as shown in FIG. 4, during the abnormality detection period Tab after the fuel cut-off is started, an output voltage of the oxygen sensor 17 is detected for each constant time and it is determined whether the detected output voltage is less than the negative voltage determination value Vth1. Each time it is determined that the detected output voltage is less than the negative voltage determination value Vth1 and is the negative voltage, the abnormality counter counts up, thus counting the negative voltage continuation time during a period it is determined that the output voltage is the negative voltage. When the value Nng of the abnormality counter reaches the time determination value Nth1, it is determined that the element crack abnormality is present in the oxygen sensor 17. In the embodiment, a count value of the abnormality counter is not cleared and accumulated even after the abnormality detection period passes, but may be cleared each time the abnormality detection period passes.

In the above processing, it is of importance to differentiate the abnormality detection period relative to the fuel cut-off period with some delay such as T1 or T2. For an accurate detection of crack abnormality, the abnormality detection condition is changed at step S130 in FIG. 3. This abnormality detection condition changing processing may be attained by the following processes (1) to (4).

Figure 5A:
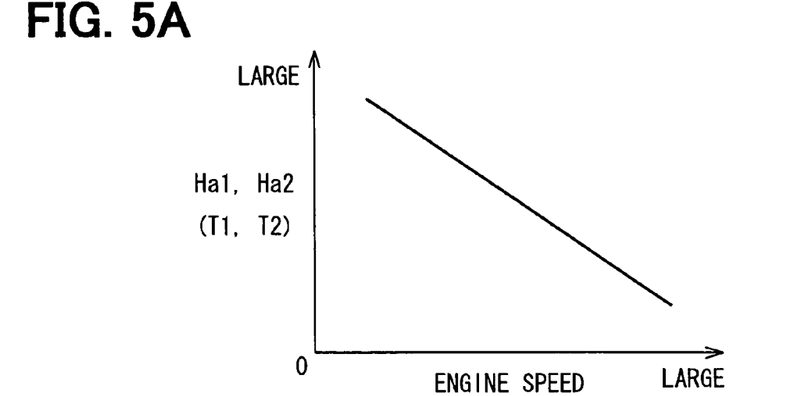
FIG. 5A is a graph showing variable setting of an abnormality detection period with respect to an engine speed.
Figure 5B:
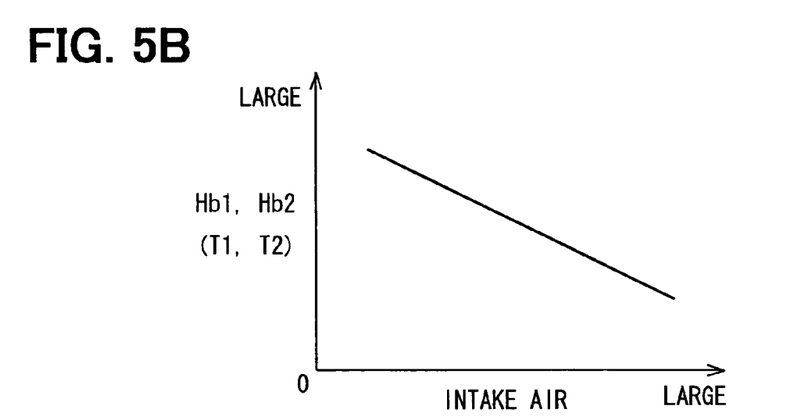
FIG. 5B is a graph showing variable setting of an abnormality detection period with respect to an intake air quantity (or throttle position)
Figure 5C:
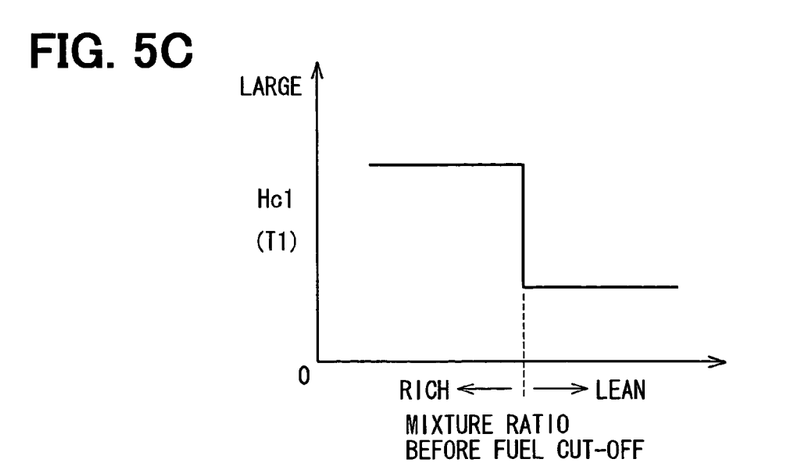
FIG. 5C is a graph showing variable setting of an abnormality detection period with respect to a mixture state immediately before the fuel cut-off.

(1) The above first delay time T1 for determining an abnormality detection period is variably defined corresponding to each of an engine rotational speed, an intake air quantity, and a state of the mixture immediately before the fuel cut-off is started, as shown in FIGS. 5A to 5C.

In detail, firstly a correction coefficient for multiplying a basic value of the first time T1 includes a correction coefficient Ha1 in accordance with an engine rotational speed, a correction coefficient Hb1 in accordance with an intake air quantity and a correction coefficient Hc in accordance with a state of the mixture.

The correction coefficient Ha1 is, as shown in FIG. 5A, stored in the ROM (not shown) of the microcomputer 31 in such a manner as to decrease corresponding to an increase of the engine rotational speed.

Likewise, the correction coefficient Hb1 is, as shown in FIG. 5B, stored in the ROM of in the microcomputer 31 in such a manner as to decrease corresponding to an increase of the intake air quantity. The correction coefficient Hc1 is, as shown in FIG. 5C, stored in the ROM of the microcomputer 31 in such a manner as to decrease more at a lean air-fuel ratio of the mixture than at a rich air-fuel ratio thereof.

The microcomputer 31 reads out an engine rotational speed, an intake air quantity and a state of the mixture detected immediately before the starting of the fuel cut-off from the RAM (not shown) and calculates the correction coefficients Ha1, Hb1 and Hc1 corresponding thereto with an interpolation calculation from the respective data maps having characteristics in FIGS. 5A to 5C. The microcomputer 31 multiplies the basic value of the first time T1 by the calculated coefficients Ha1, Hb1 and Hc1, thereby setting the first time T1 used for the determination at next step S140.

Therefore, the first time T1 decreases as an engine rotational speed increases and decreases as intake air quantity increases. In addition, the first time T1 is set to decrease more at a lean air-fuel ratio of the mixture than at a rich air-fuel ratio thereof.

As shown in a parentheses of an abscissa axis in FIG. 5B, a correction coefficient Hb1 may be determined in accordance with a throttle position instead of an intake air quantity. On the other hand, with respect to an engine rotational speed and an intake air quantity or a throttle position for determining the correction coefficients Ha1 and Hb1, a detection value thereof at the time of starting the fuel cut-off may be used.

(2) The above second delay time T2 for determining an abnormality detection period is variably defined corresponding to each of an engine rotational speed and an intake air quantity immediately before the fuel cut-off is ended, as shown in FIGS. 5A and 5B.

In detail, firstly correction coefficients for multiplying a basic value of the second time T2 include a correction coefficient Ha2 in accordance with an engine rotational speed and a correction coefficient Hb2 in accordance with an intake air quantity.

The correction coefficient Ha2 is, as shown in FIG. 5A, stored in the ROM of the microcomputer 31 in such a manner as to decrease corresponding to an increase of the engine rotational speed.

Similarly, the correction coefficient Hb2 is, as shown in FIG. 5B, stored in the ROM (not shown) of the microcomputer 31 in such a manner as to decrease corresponding to an increase of the intake air quantity.

The microcomputer 31 reads out an engine rotational speed and an intake air quantity detected immediately before the ending of the fuel cut-off from the RAM and calculates correction coefficients Ha2 and Hb2 corresponding thereto with an interpolation calculation from the respective data maps having characteristics in FIGS. 5A and 5B. The microcomputer 31 multiplies the basic value of the second time T2 by the calculated correction coefficients Ha2 and Hb2, thereby setting the second time T2 used for the determination at next step S140.

Therefore, the second time T2 decreases as an engine rotational speed increases and decreases as intake air quantity increases.

As shown in a parentheses of an abscissa axis in FIG. 5B, a correction coefficient Hb2 may be determined in accordance with a throttle position instead of an intake air quantity. On the other hand, with respect to an engine rotational speed and an intake air quantity or a throttle position for determining the correction coefficients Ha2 and Hb2, a detection value thereof at the time of ending the fuel cut-off may be used.

Figure 6A:
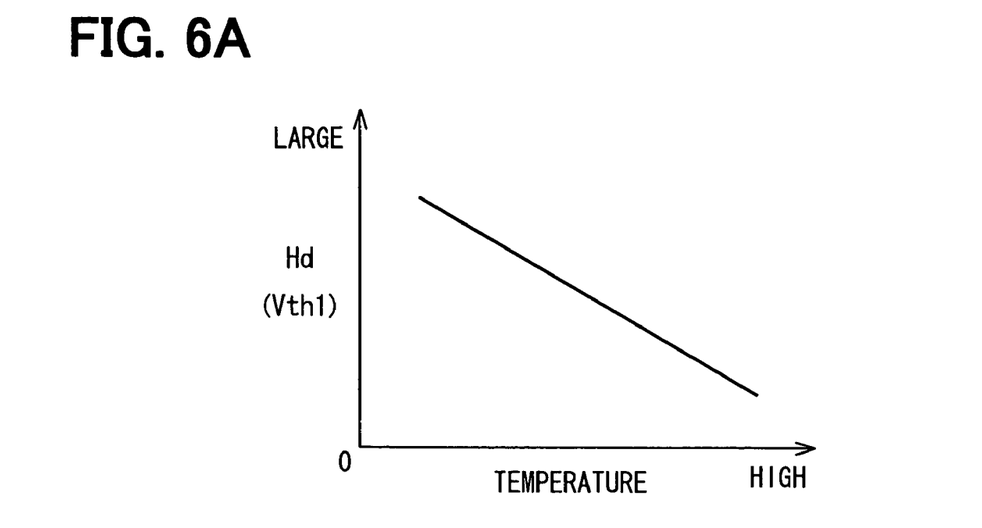
FIG. 6A is a graph showing variable setting of a negative voltage determination value with respect to a sensor temperature.
Figure 6B:
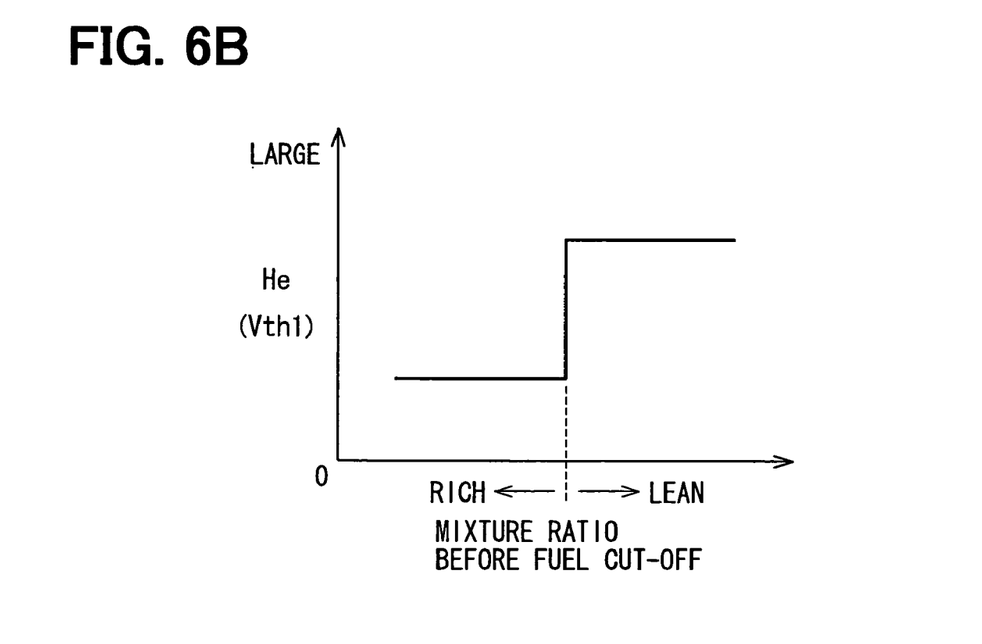
FIG. 6B is a graph showing variable setting of a negative voltage determination value with respect to a mixture state immediately before the fuel cut-off.

(3) A negative voltage determination value Vth1 used at step S150 is variably defined corresponding to each of a temperature of the oxygen sensor 17 (sensor temperature) and a state of the mixture immediately before the fuel cut-off is started, as shown in FIGS. 6A and 6B.

In detail, firstly correction coefficients for multiplying a basic value of the negative voltage determination value Vth1 include a correction coefficient Hd in accordance with a sensor temperature and a correction coefficient He in accordance with a state of the mixture.

The correction coefficient Hd is, as shown in FIG. 6A, stored in the ROM of the microcomputer 31 in such a manner as to increase corresponding to a decrease of the sensor temperature.

The correction coefficient He is, as shown in FIG. 6B, stored in the ROM of the microcomputer 31 in such a manner as to have a value greater at a lean air-fuel ratio of the mixture than at a rich air-fuel ratio thereof.

The microcomputer 31 takes in a sensor temperature and a state of the mixture detected immediately before the starting of the fuel cut-off from the RAM and calculates correction coefficients Hd and He corresponding thereto with an interpolation calculation from the respective data maps having characteristics in FIGS. 6A and 6B. The microcomputer 31 multiplies the basic value of the negative voltage determination value Vth1 by the calculated correction coefficients Hd and He, thereby setting the negative voltage determination value Vth1 used for the determination at step S150. The sensor temperature may be calculated from a count value of element impedance of the oxygen sensor 17.

Therefore, the negative voltage determination value Vth1 is set to increase as the sensor temperature decreases and have a value greater at a lean air-fuel ratio of the mixture than at a rich air-fuel ratio thereof.

In addition, with respect to a sensor temperature for determining the correction coefficient Hd, a detection value thereof at the time of starting the fuel cut-off may be used. On the other hand, the negative voltage determination value Vth1 may be variably set in real time in accordance with a sensor temperature even during the abnormality detection period.

Figure 7:
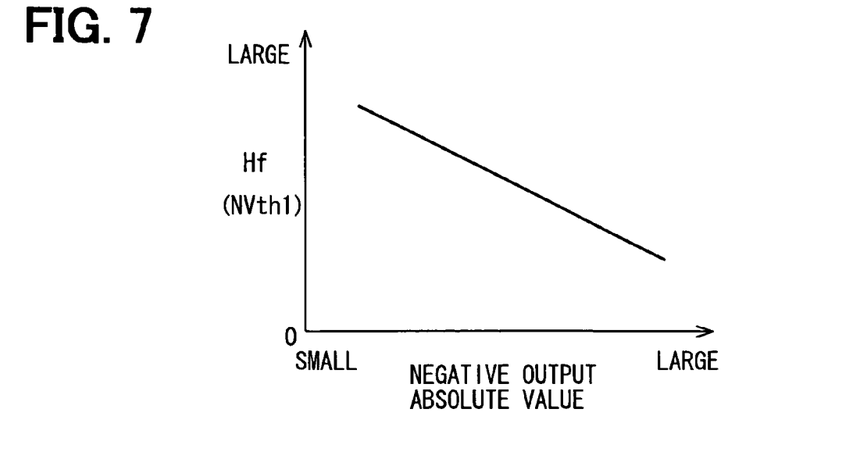
FIG. 7 is a graph showing variable setting of an accumulating time determination value with respect to a negative voltage output of an oxygen sensor.

(4) A negative voltage continuation time determination value Nth1 used for determination at step S170 is, as shown in FIG. 7, variably defined corresponding to each of a magnitude of an output voltage of the oxygen sensor 17 (i.e., a magnitude of a negative voltage outputted from the oxygen sensor 17 and hereinafter referred to as negative voltage output) at a point when it is determined at step S150 that the output voltage of the oxygen sensor 17 is less than the negative voltage determination value Vth1.

In detail, firstly a correction coefficient for multiplying a basic value of the time determination value Nth1 includes a correction coefficient Hf in accordance with a negative voltage output of the oxygen sensor 17.

The correction coefficient Hf is, as shown in FIG. 7, stored in the ROM of the microcomputer 31 in such a manner as to decrease corresponding to an increase of an absolute value of the negative voltage output.

Accordingly, when the microcomputer 31 first determines at step S150 that the output voltage of the oxygen sensor 17 is less than the negative voltage determination value Vth1, the microcomputer 31 stores the then-output voltage of the oxygen sensor 17 as the first negative voltage output in the RAM. At next step S130 the microcomputer 31 reads out the stored first negative voltage output from the RAM and calculates a correction coefficient Hf corresponding to the read-out negative voltage output with an interpolation calculation from the data map having the characteristic in FIG. 7. The microcomputer 31 multiplies the basic value of the time determination value Nth1 by the calculated correction coefficient Hf, thereby setting the time determination value Nth1 used for the determination at step S170.

Therefore, the time determination value Nth1 is set to decrease corresponding to an increase of an absolute value of the negative voltage output from the oxygen sensor 17. In addition, an initial value of the time determination value Nth1 (i.e., a value until at step S130 the time determination value Nth1 is set as a value corresponding to the negative voltage output of the oxygen sensor 17) is the maximum value within a variable range According to the ECU 1 in the above embodiment, even if a period (negative voltage generation period) in which an output voltage of the oxygen sensor 17 is a negative voltage, caused by occurrence of element crack abnormality in the oxygen sensor 17, changes by each of an engine rotational speed, a throttle position and a state of the mixture, the abnormality detection period can be accurately adjusted to the actual negative voltage generation period by the above processes (1) and (2) in the abnormality detection condition changing processing executed at step S130 in FIG. 3. Accordingly, the element crack abnormality of the oxygen sensor 17 can be quickly and accurately detected without unnecessarily executing the determination processing at step S150.

In particular, in the embodiment the abnormality detection period does not necessarily end at the time of the fuel cut-off ending, but the second time T2 as a period from when the fuel cut-off ends to when the abnormality detection period ends is variably set. Therefore, detection accuracy of the element crack abnormality can be improved by effectively extending the abnormality detection period. This is because even if the fuel cut-off ends, an air-fuel ratio of the mixture near the oxygen sensor 17 remains to be extremely lean for a certain period after that, thereby possibly producing a negative voltage and the negative voltage from the oxygen sensor 17 can be monitored for that period (period of the second time T2).

Further, according to the ECU 1 of the embodiment, when the element crack abnormality occurs, a value of the negative voltage (negative voltage output) outputted from the oxygen sensor 17 changes by each of the sensor temperature and the state of the mixture before the fuel cut-off. However, a negative voltage determination value Vth1 can be set as an appropriate value with which it can be determined properly whether an output voltage of the oxygen sensor 17 is a negative voltage by the above process (3) in the abnormality detection condition changing processing executed at step S130 in FIG. 3. Accordingly, determination accuracy as to whether the output voltage of the oxygen sensor 17 is the negative voltage can be improved, leading to quick and accurate detection of element crack abnormality in the oxygen sensor 17.

Further, according to the ECU 1 of the embodiment, a magnitude and a negative voltage continuation time of the negative voltage outputted from the oxygen sensor 17 change with the degree of the element crack. However, even in this case, a negative voltage continuation time determination value Nth1 can be set as an appropriate value in accordance with a magnitude of the negative voltage by the above process (4) in the abnormality detection condition changing processing executed at step S130 in FIG. 3. Therefore, even if the degree of the element crack of the oxygen sensor 17 differs, the element crack abnormality can be quickly and accurately detected.

Next, in the ECU 1 of the embodiment, other processing executed by the microcomputer 31 for quickly and accurately detecting element crack abnormality of the oxygen sensor 17 will be explained with reference to FIGS. 8 to 10.

Figure 8:
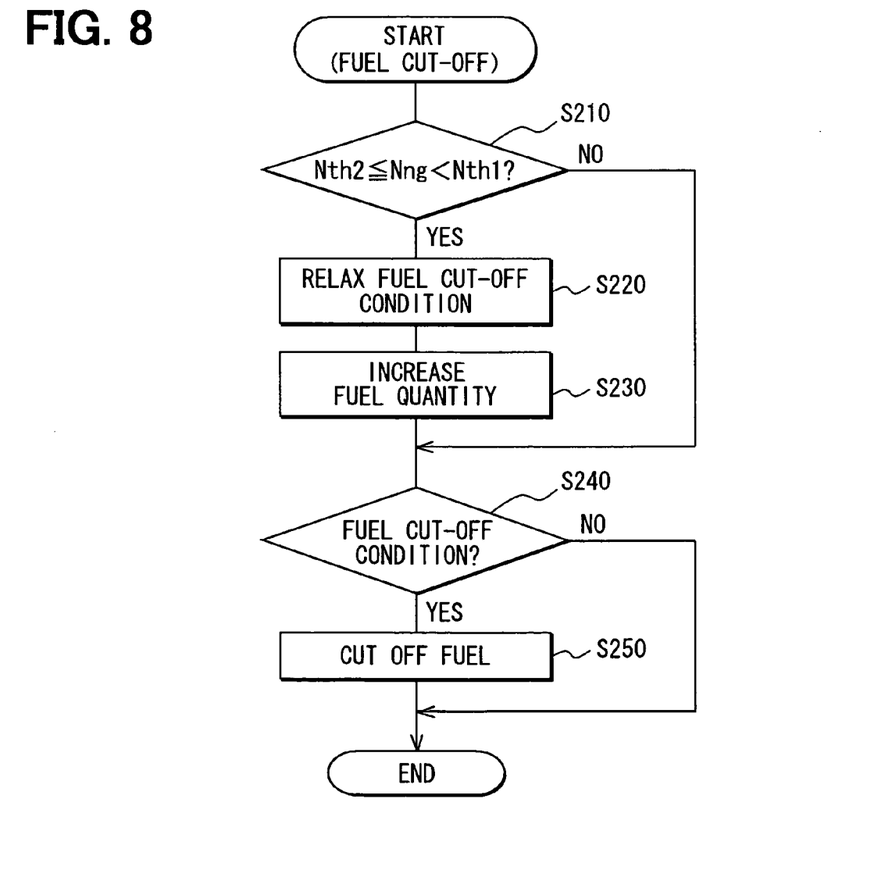
FIG. 8 is a flow chart showing fuel cut-off control processing.

First, FIG. 8 is a flow chart showing fuel cut-off control processing, which is executed for each constant cycle when the fuel cut-off is not effected.

As shown in FIG. 8, when the microcomputer 31 starts execution of the fuel cut-off control processing, first it is determined at step S210 whether a value Nab of the abnormality counter to be counted up at step S160 in FIG. 3 is more than a specified value Nth2 smaller than the time determination value Nth1 and also is smaller than the time determination value Nth1 (i.e., Nth2≦abnormality counter (Nng)<Nth1).

When it is determined at step S210 that "Nth2≦abnormality counter<Nth1" is not established, the process proceeds to step S240. On the other hand, when it is determined at step S210 that "Nth2≦abnormality counter<Nth1" is established, the process proceeds to step S220, wherein the above fuel cut-off condition (execution condition of the fuel cut-off) is relaxed, thus creating a state for more likely executing the fuel cut-off. In more detail, a fuel cut-off rotational speed NC1 in the fuel cut-off condition for fuel saving is altered to a value smaller than an initial setting value thereof and a fuel cut-off rotational speed NC2 in the fuel cut-off condition for engine protection is altered to a value smaller than an initial setting value thereof.

Further, at step S230, a fuel injection quantity of fuel supplied to the engine 3 is corrected, specifically increased. For instance, a constant correction value of the fuel or a constant ratio of the fuel is added to a fuel injection quantity calculated in accordance with an operating condition of the engine 3. Thereafter, the process proceeds to step S240.

At step S240 it is determined whether the fuel cut-off condition is met. When it is determined that the fuel cut-off condition is not met, the fuel cut-off control processing ends.

When it is determined that the fuel cut-off condition is met, the process proceeds to step S250, wherein the fuel cut-off is effected. Thereafter, the fuel cut-off control processing ends. In addition, when the fuel cut-off is effected at step S250, the fuel cut-off state continues until the fuel resumption condition is met.

According to such fuel cut-off control processing, in a case where a value of the abnormality counter value Nng is less than the time determination value Nth1 and more than the specified value Nth2, whereby it is considered that the element crack abnormality possibly occurs in the oxygen sensor 17 (step S210: YES), the fuel cut-off condition is relaxed and thereafter, the fuel cut-off is more likely to be executed (step S220). Therefore, opportunities for determining whether an output voltage of the oxygen sensor 17 is a negative voltage are to be increased, thus improving abnormality detection capabilities.

Further, in a case where it is considered that the element crack abnormality of the oxygen sensor 17 possibly occurs (step S210: YES), a fuel injection quantity to the engine 3 is corrected for an increase of fuel (step S230). Therefore, when the element crack abnormality really occurs, the negative voltage from the oxygen sensor 17 is more likely to be outputted at the next fuel cut-off time point. That is, an absolute value of the negative voltage outputted from the oxygen sensor 17 increases and also the output negative voltage continuation time of the negative voltage is lengthened. As a result, the abnormality detection capabilities by the processing in FIG. 3 are further improved.

However, the processes at steps S220 and S230 affect drivability and exhaust emission performance of a vehicle. Therefore, the specified value N th2 may be defined considering a balance with an improvement of the abnormality detection capabilities. That is, if importance is placed more on the improvement of the abnormality detection capabilities, the specified value Nth2 may be defined as a value as small as possible (e.g., "1"). On the other hand, if importance is placed more on avoidance of adverse affect to the drivability and the exhaust emission performance of the vehicle, the specified value Nth2 may be defined as a value as close to the time determination value Nth1 as possible.

Figure 9:
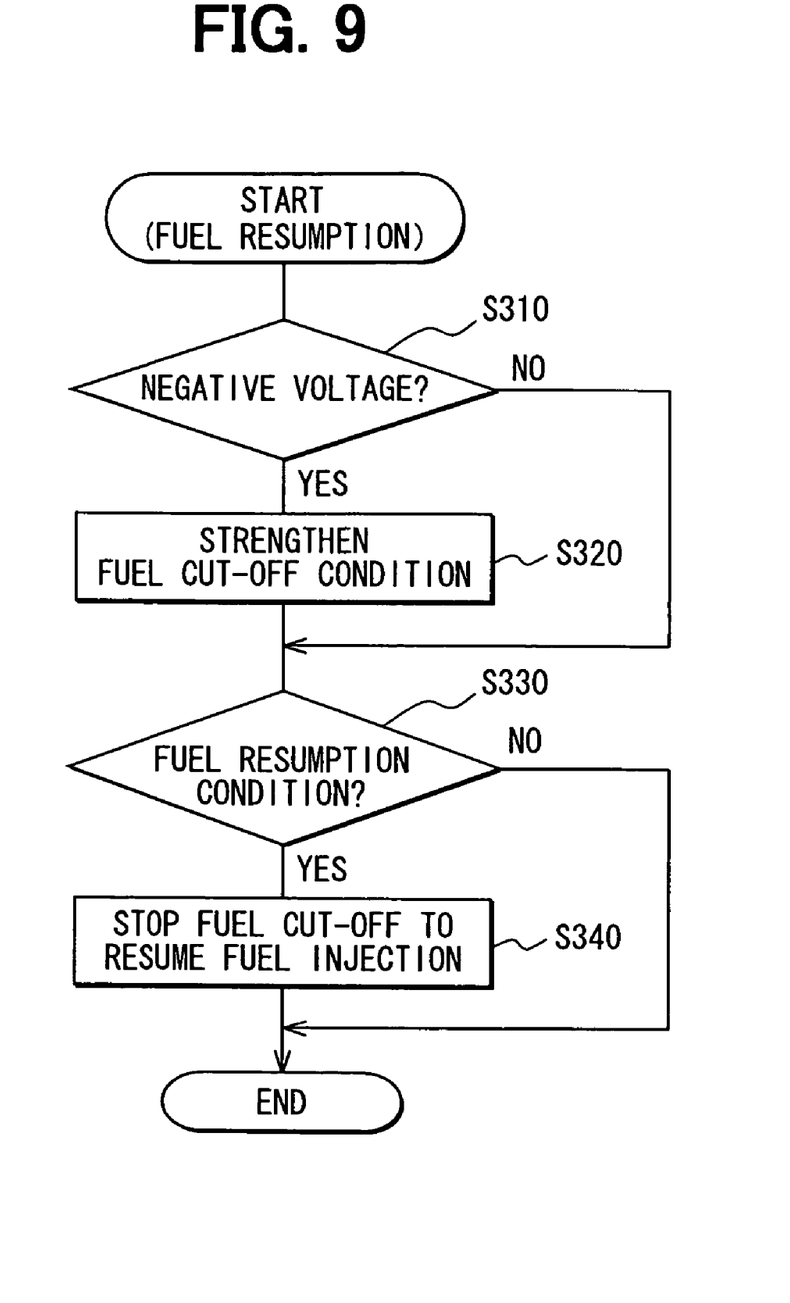
FIG. 9 is a flow chart showing fuel resumption control processing.

Next, FIG. 9 is a flow chart showing the fuel resumption control processing. The fuel resumption control processing is executed for each constant time when the fuel cut-off is effected.

As shown in FIG. 9, when the microcomputer 31 starts execution of the fuel resumption control processing, first at step S310 it is determined whether it is determined at step S150 in FIG. 3 during the fuel cut-off at this time that "an output voltage of the oxygen sensor 17≦Vth1" is established (i.e., it is determined that the output voltage of the oxygen sensor 17 is a negative voltage). When it is determined at step S150 that this relation is not established, the process proceeds to step S330.

In a case where it is determined at step S150 in FIG. 3 during the fuel cut-off that the expression is established (step S310: YES), the process proceeds to step S320, wherein the above fuel cut-off condition is strengthened, thereby more likely continuing execution of the fuel cut-off. In more detail, a fuel resumption rotational speed NR1 in the fuel resumption condition for fuel saving is altered to a value smaller than an initial setting value thereof and a fuel resumption rotational speed NR2 in the fuel cut-off condition for engine protection is altered to a value smaller than an initial setting value thereof. Thereafter, the process proceeds to step S330.

At step S330, it is determined whether the fuel resumption condition corresponding to the present fuel cut-off is met. When it is determined that the fuel resumption condition is not met, the fuel resumption control processing ends.

Further, when it is determined at step S330 that the fuel resumption condition is met, the process proceeds to step S340. At step S340, the fuel resumption processing for stopping the fuel cut-off (i.e., the engine state returns to a state for injecting fuel to the engine 3) is executed. Thereafter, the fuel resumption control processing ends.

According to such fuel resumption control processing, in a case where it is determined at step S150 in FIG. 3 during the fuel cut-off that an output voltage of the oxygen sensor 17 is a negative voltage, whereby it is considered that the element crack abnormality possibly occurs (step S310: YES), the fuel resumption condition is strengthened, thereby more likely continuing execution of the fuel cut-off (step S320). Therefore, opportunities for determining at step S150 in FIG. 3 whether an output voltage of the oxygen sensor 17 is a negative voltage (the time for confirming whether the element crack abnormality occurs) are to be increased, thus improving abnormality detection capabilities.

Figure 10:
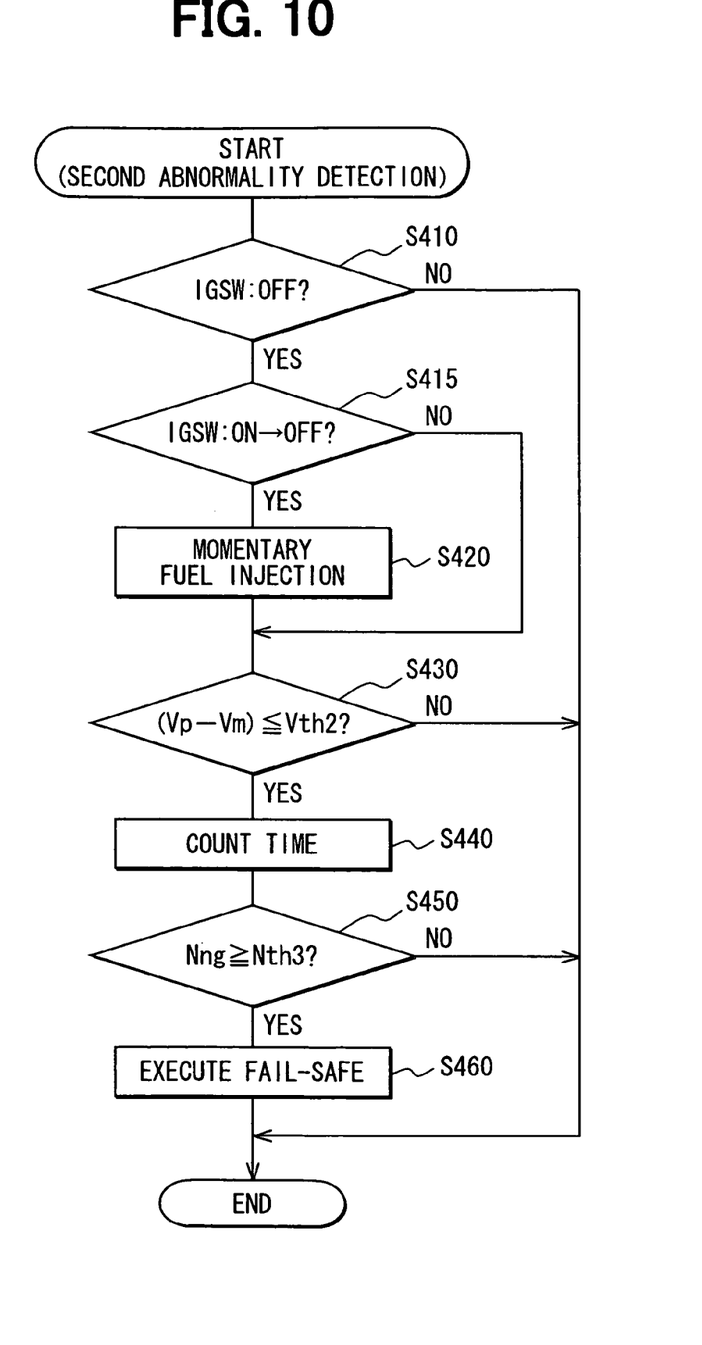
FIG. 10 is a flow chart showing second abnormality detection processing.

Next, FIG. 10 is a flow chart showing second abnormality detection processing. The second abnormality detection control processing is also executed for each constant time.

As shown in FIG. 10, when the microcomputer 31 starts execution of the second abnormality detection processing, first at step S410 it is determined whether an ignition switch (IGSW) is turned off. When it is determined that the ignition switch is not turned off (turned on), the second abnormality detection processing ends.

When it is determined at step S410 that the ignition switch is turned off, the process proceeds to step S415 and determines whether the process at this time is the first time process after the ignition switch has changed from ON to OFF.

When a determination of "NO" is made at step S415, the process proceeds to step S430. However, when a determination of "YES" is made at step S415 (i.e., immediately after the ignition switch has changed from ON to OFF), the process proceeds to step S420 to inject fuel in the engine 3 only for a certain time, that is, momentary forcible fuel injection is carried out. Thereafter, the process proceeds to step S430.

At step S430, an output voltage (Vp−Vm) of the oxygen sensor 17 is calculated in the same way as at step S150 in FIG. 3. It is also determined whether the output voltage is less than the negative voltage determination value Vth2. When the output voltage is not less than the negative voltage determination value Vth2, the second abnormality detection processing ends. When the output voltage is less than the negative voltage determination value Vth2, it is determined that the output voltage is a negative voltage and the process proceeds to step S440.

At step S440, the abnormality counter is counted up and next at step S450. It is determined whether a value Nng of the abnormality counter is more than a third negative voltage continuation time determination value Nth3. When it is determined that the value of the abnormality counter is not more than the time determination value Nth3, the second abnormality detection processing ends. When it is determined that the value of the abnormality counter is more than the negative voltage continuation time determination value Nth3, it is determined that the element crack abnormality of the oxygen sensor 17 occurs, and the process proceeds to step S460.

At step S460, the failsafe processing similar to that at step S180 in FIG. 3 is executed and thereafter, the second abnormality detection processing ends.

However, more or less time takes from a point the ignition switch is turned off to a point the engine stops. Therefore, the processes after step S430 are executed a plurality of times within that period of time. The negative voltage determination value Vth2 at step S430 and the negative voltage continuation time determination value Nth3 at step S450 are determination values set separately from the negative voltage determination value Vth1 and the time determination value Nth1 in the abnormality detection processing in FIG. 3. Further, in the embodiment the abnormality counter which is counted up and a magnitude of which is determined at steps S440 and S450 is an abnormality counter different from the abnormality counter to be counted up at step S160 in FIG. 3, but may be the same as that.

That is, in the second abnormality detection processing in FIG. 10, fuel is injected to the engine 3 only once for a period from a point the ignition switch is turned off to a point the engine 3 stops (step S420). Thereby, thereafter, even for a stop delay period until the engine stops, the state similar to that at the time of fuel cut-off during the operating of the engine 3 is provided to monitor whether the output voltage of the oxygen sensor 17 is a negative voltage (step S430). When a value of the abnormality counter corresponding to a count value of the negative voltage continuation time for a period when it is determined that the output voltage of the oxygen sensor 17 is a negative voltage is more than the time determination value Nth3, it is determined that the element crack abnormality occurs in the oxygen sensor 17 (step S450: YES→step S460).

In addition, by means of execution of such second abnormality detection processing, it can be confirmed whether the element crack abnormality of the oxygen sensor 17 occurs not only when the fuel cut-off is effected, but also when the ignition switch is turned off. As a result, the element crack abnormality of the oxygen sensor 17 can be quickly and accurately detected.

In the above embodiment, the process at step S150 in FIG. 3 operates as a negative voltage detection section, the processes at steps S160 and S170 in FIG. 3 and the processes at steps S440 and S450 in FIG. 10 operate as an abnormality determination section and the process at step S130 in FIG. 3 operates as an abnormality detection condition changing section.

The processes at steps S210 and S220 in FIG. 8 operates as a fuel cut-off condition relaxation section, the processes at steps S210 and S230 in FIG. 8 operate as a fuel injection quantity correction section and the processes at steps S310 and S320 in FIG. 9 operate as a fuel resumption condition strengthening section.

The process at step S420 among each process in FIG. 10 operates as a forcible fuel injection section and the process at step S430 thereof operates as a second negative voltage detection section.

While only the selected preferred embodiments have been chosen to illustrate the present invention, it will be apparent to those skilled in the art from this disclosure that various changes and modifications can be made therein without departing from the scope of the invention.

What is claimed is:

1. An element crack detecting apparatus for an oxygen sensor which is disposed in an exhaust system in an engine and has an oxygen sensing element, an exhaust-side electrode and an atmosphere-side electrode, the detecting apparatus comprising:
- a negative voltage detection means for detecting a potential difference between the exhaust-side electrode and the atmosphere-side electrode as an output voltage, the negative voltage detector being used in an engine control apparatus for determining a fuel injection quantity to the engine based upon a detection value to determine whether the output voltage is a negative voltage for an abnormality detection period after a fuel cut-off to the engine is started during operation of the engine;
- abnormality determination means, which determines whether an element crack abnormality is present in the oxygen sensor based upon a determination result of the negative voltage detector; and
- abnormality detection condition setting means for allowing the abnormality determination means to start determining the element crack abnormality after a start of fuel cut-off to the engine.

2. The element crack detecting apparatus according to claim 1, wherein:
the abnormality detection condition setting means variably sets a start time of determining the element crack abnormality relative to the start of fuel cut-off to the engine.

3. The element crack detecting apparatus according to claim 1, wherein:
the abnormality detection condition setting means variably sets an abnormality detection period in accordance with an operating condition of the engine.

4. The element crack detecting apparatus according to claim 3, wherein:
the abnormality detection condition setting means variably sets an abnormality detection period in accordance with a rotational speed of the engine.

5. The element crack detecting apparatus according to claim 4, wherein:
the abnormality detection period is a period from a point a first time elapses after the fuel cut-off is started to a point a second time elapses after the fuel cut-off is ended; and
the abnormality detection condition setting means variably sets at least one of the first time and the second time in accordance with the rotational speed of the engine.

6. The element crack detecting apparatus according to claim 3, wherein:
the abnormality detection condition setting means variably sets the abnormality detection period in accordance with a state of an air-fuel mixture immediately before the fuel cut-off is started.

7. The element crack detecting apparatus according to claim 6, wherein:
the abnormality detection period is a period from a point a first time elapses after the fuel cut-off is started to a point a second time elapses after the fuel cut-off is ended; and
the abnormality detection condition setting means variably sets the first time in accordance with the state of the mixture immediately before the fuel cut-off is started.

8. The element crack detecting apparatus according to claim 3, wherein:
the abnormality detection condition setting means variably sets an abnormality detection period in accordance with a throttle position of the engine.

9. The element crack detecting apparatus according to claim 8, wherein:
the abnormality detection period is a period from a point a first time elapses after the fuel cut-off is started to a point a second time elapses after the fuel cut-off is ended; and
the abnormality detection condition setting means variably sets at least one of the first time and the second time in accordance with a throttle position of the engine.

10. The element crack detecting apparatus according to claim 3, wherein:
the abnormality detection condition setting means variably sets an abnormality detection period in accordance with an intake air quantity of the engine.

11. The element crack detecting apparatus according to claim 10, wherein:
the abnormality detection period is a period from a point a first time elapses after the fuel cut-off is started to a point a second time elapses after the fuel cut-off is ended; and
the abnormality detection condition setting means variably sets at least one of the first time and the second time in accordance with the intake air quantity of the engine.

12. An element crack detecting apparatus for an oxygen sensor, which is disposed in an exhaust system in an engine and has an oxygen sensing element, an exhaust-side electrode and an atmosphere-side electrode, the detecting apparatus comprising:
- a negative voltage detection means for detecting a potential difference between the exhaust-side electrode and the atmosphere-side electrode as an output voltage, the negative voltage detector being used in an engine control apparatus for determining a fuel injection quantity to the engine based upon a detection value to determine whether the output voltage is a negative voltage for an abnormality detection period after a fuel cut-off to the engine is started during operation of the engine;
- abnormality determination means, which determines whether an element crack abnormality is present in the oxygen sensor based upon a determination result of the negative voltage detector; and
- abnormality detection condition setting means, which variably sets a negative voltage determination value with which the negative voltage detector determines whether the output voltage of the oxygen sensor is a negative voltage, in accordance with an operating condition of the engine.

13. The element crack detecting apparatus according to claim 12, wherein:
the abnormality detection condition setting means variably sets the negative voltage determination value in accordance with a temperature of the oxygen sensor.

14. The element crack detecting apparatus according to claim 12, wherein:
the abnormality detection condition setting means variably sets the negative voltage determination value in accordance with a state of a mixture immediately before the fuel cut-off is started.

15. An element crack detecting apparatus for an oxygen sensor, which is disposed in an exhaust system in an engine and has an oxygen sensing element, an exhaust-side electrode and an atmosphere-side electrode, the detecting apparatus comprising:

a negative voltage detection means for detecting a potential difference between the exhaust-side electrode and the atmosphere-side electrode as an output voltage, the negative voltage detector being used in an engine control apparatus for determining a fuel injection quantity to the engine based upon a detection value to determine whether the output voltage is a negative voltage for an abnormality detection period after a fuel cut-off to the engine is started during operation of the engine;

abnormality determination means, which determines whether an element crack abnormality is present in the oxygen sensor based upon a determination result of the negative voltage detector, wherein the abnormality determination means counts a negative voltage continuation time for a period in which the negative voltage detector determines that the output voltage of the oxygen sensor is the negative voltage and also determines whether the negative voltage continuation time reaches a negative voltage continuation time determination value, thereby determining that the element crack abnormality is present when it is determined that the negative voltage continuation time reaches the negative voltage continuation time determination value; and abnormality detection condition setting means variably sets the negative voltage continuation time determination value in accordance with a magnitude of the negative voltage outputted from the oxygen sensor.

16. An element crack detecting apparatus for an oxygen sensor, which is disposed in an exhaust system in an engine and has an oxygen sensing element, an exhaust-side electrode and an atmosphere-side electrode, the detecting apparatus comprising:

a negative voltage detection means for detecting a potential difference between the exhaust-side electrode and the atmosphere-side electrode as an output voltage, the negative voltage detector being used in an engine control apparatus for determining a fuel injection quantity to the engine based upon a detection value to determine whether the output voltage is a negative voltage for an abnormality detection period after a fuel cut-off to the engine is started during operation of the engine;

abnormality determination means, which determines whether an element crack abnormality is present in the oxygen sensor based upon a determination result of the negative voltage detector, wherein the abnormality determination means counts a negative voltage continuation time for a period in which the negative voltage detector determines that the output voltage of the oxygen sensor is the negative voltage and also determines whether the negative voltage continuation time reaches a negative voltage continuation time determination value, thereby determining that the element crack abnormality is present when it is determined that the negative voltage continuation time reaches the negative voltage continuation time determination value, wherein the abnormality determination means counts a negative voltage continuation time for a period in which the negative voltage detector determines that the output voltage of the oxygen sensor is the negative voltage and also determines whether the negative voltage continuation time reaches a negative voltage continuation time determination value, thereby determining that the element crack abnormality occurs in the oxygen sensor when it is determined that the negative voltage continuation time reaches the negative voltage continuation time determination value; and fuel cut-off condition relaxing means, which relaxes an execution condition of the fuel cut-off when the negative voltage continuation time is more than a specified value smaller than the negative voltage continuation time determination value, thereby more frequently effecting the fuel cut-off.

17. An element crack detecting apparatus for an oxygen sensor, which is disposed in an exhaust system in an engine and has an oxygen sensing element, an exhaust-side electrode and an atmosphere-side electrode, the detecting apparatus comprising:

a negative voltage detection means for detecting a potential difference between the exhaust-side electrode and the atmosphere-side electrode as an output voltage, the negative voltage detector being used in an engine control apparatus for determining a fuel injection quantity to the engine based upon a detection value to determine whether the output voltage is a negative voltage for an abnormality detection period after a fuel cut-off to the engine is started during operation of the engine;

abnormality determination means, which determines whether an element crack abnormality is present in the oxygen sensor based upon a determination result of the negative voltage detector, wherein the abnormality determination means counts a negative voltage continuation time for a period in which the negative voltage detector determines that the output voltage of the oxygen sensor is the negative voltage and also determines whether the negative voltage continuation time reaches a negative voltage continuation time determination value, thereby determining that the element crack abnormality is present when it is determined that the negative voltage continuation time reaches the negative voltage continuation time determination value, wherein the abnormality determination means counts a negative voltage continuation time for a period in which the negative voltage detector determines that the output voltage of the oxygen sensor is the negative voltage and also determines whether the negative voltage continuation time reaches a negative voltage continuation time determination value, thereby determining that the element crack abnormality occurs in the oxygen sensor when it is determined that the negative voltage continuation time reaches the negative voltage continuation time determination value; and fuel injection quantity correction means which increases an injection quantity of fuel supplied to the engine by the engine control apparatus when the negative voltage continuation time is more than a specified value smaller than the negative voltage continuation time determination value.

18. An element crack detecting apparatus for an oxygen sensor, which is disposed in an exhaust system in an engine and has an oxygen sensing element, an exhaust-side electrode and an atmosphere-side electrode, the detecting apparatus comprising:

a negative voltage detection means for detecting a potential difference between the exhaust-side electrode and the atmosphere-side electrode as an output voltage, the negative voltage detector being used in an engine control apparatus for determining a fuel injection quantity to the engine based upon a detection value to determine whether the output voltage is a negative voltage for an abnormality detection period after a fuel cut-off to the engine is started during operation of the engine;

abnormality determination means, which determines whether an element crack abnormality is present in the oxygen sensor based upon a determination result of the negative voltage detector, wherein the abnormality determination means counts a negative voltage continuation time for a period in which the negative voltage detector determines that the output voltage of the oxygen sensor is the negative voltage and also determines whether the negative voltage continuation time reaches a negative voltage continuation time determination value, thereby determining that the element crack abnormality is present when it is determined that the negative voltage continuation time reaches the negative voltage continuation time determination value, wherein the abnormality determination means counts a negative voltage continuation time for a period in which the negative voltage detector determines that the output voltage of the oxygen sensor is the negative voltage and also determines whether the negative voltage continuation time reaches a negative voltage continuation time determination value, thereby determining that the element crack abnormality occurs in the oxygen sensor when it is determined that the negative voltage continuation time reaches the negative voltage continuation time determination value; and fuel resumption condition strengthening means which strengthens a resumption condition for resuming an engine condition from a state of the fuel cut-off back to a state to inject fuel to the engine when it is determined that the output voltage of the oxygen sensor is the negative voltage during effecting the fuel cut-off by the negative voltage detector, thereby more likely continuing the fuel cut-off at this time.

19. An element crack detecting apparatus for an oxygen sensor, which is disposed in an exhaust system in an engine and has an oxygen sensing element, an exhaust-side electrode and an atmosphere-side electrode, the detecting apparatus comprising:

a negative voltage detection means for detecting a potential difference between the exhaust-side electrode and the atmosphere-side electrode as an output voltage, the negative voltage detector being used in an engine control apparatus for determining a fuel injection quantity to the engine based upon a detection value to determine whether the output voltage is a negative voltage for an abnormality detection period after a fuel cut-off to the engine is started during operation of the engine;

abnormality determination means, which determines whether an element crack abnormality is present in the oxygen sensor based upon a determination result of the negative voltage detector;

forcible fuel injection means, which injects the fuel to the engine for a period from a point an ignition switch of a vehicle in which the engine is mounted is turned off to a point the engine stops; and a second negative voltage detector which determines whether the output voltage of the oxygen sensor is the negative voltage after the fuel injection by the forcible fuel injection means is completed, wherein:

the abnormality determination means determines whether the element crack abnormality in the oxygen sensor occurs based upon the determination result of the negative voltage detector and the determination result of the second negative voltage detector.

20. The element crack detecting apparatus according to claim 19, further comprising:

activated state determination means which determines whether the oxygen sensor is in an activated state; and reference voltage changing means, which makes a potential of the exhaust-side electrode of the oxygen sensor equal to the ground level until the activated state determination means determines that the oxygen sensor is in the activated state and which increases the potential of the exhaust-side electrode of the oxygen sensor to a potential higher than the ground level when the activated state determination means determines that the oxygen sensor is in the activated state.

21. An element crack detecting method for an oxygen sensor, which is disposed in an exhaust system in an engine and has an oxygen sensing element, an exhaust-side electrode and an atmosphere-side electrode, the detecting method comprising:

detecting an output signal developed between the electrodes, the output signal being used in an engine control apparatus for feedback-controlling fuel injection to the engine based on the output signal; and determining an element crack abnormality based on a change of polarity of the output signal, in which a potential of the exhaust-side electrode becomes higher than that of the atmosphere-side electrode.

22. The element crack detecting method according to claim 21, wherein:

the determining performs the element crack abnormality in a period of a fuel cut-off to the engine.

23. The element crack detecting method according to claim 22, further comprising:

delaying a start of determination of the element crack abnormality relative to a start of the fuel cut-off to the engine.

24. The element crack detecting method according to claim 22, further comprising:

the delaying sets a delay period variably in accordance with an engine operating condition.

25. The element crack detecting method according to claim 21, wherein:

the determining determines the element crack abnormality when the change of polarity continues for more than a predetermined period.

26. The element crack detecting method according to claim 22, further comprising:

starting a forced fuel supply to the engine again in response to a turn-off of an ignition switch of the engine, wherein the determining performs a determination of the element crack abnormality after the forced fuel supply is terminated.

* * * * *